(12) United States Patent
Fava et al.

(10) Patent No.: US 6,794,194 B2
(45) Date of Patent: Sep. 21, 2004

(54) METHOD FOR MEASURING HEMOGLOBIN CONCENTRATION (HGB) IN THE BLOOD IN A CIRCUIT OF A DIALYSIS MACHINE, MEASURING DEVICE AND CIRCUIT FOR THE APPLICATION OF THE METHOD

(75) Inventors: Massimo Fava, Mirandola (IT);
Annalisa Delnevo, Correggio (IT);
Francesco Paolini, Modena (IT)

(73) Assignee: Gambro Dasco SpA, Medolla (IT)

( * ) Notice: Subject to any disclaimer, the term of this patent is extended or adjusted under 35 U.S.C. 154(b) by 0 days.

(21) Appl. No.: 10/258,117

(22) PCT Filed: Feb. 26, 2002

(86) PCT No.: PCT/IB02/00563
§ 371 (c)(1),
(2), (4) Date: Oct. 21, 2002

(87) PCT Pub. No.: WO02/071039
PCT Pub. Date: Sep. 12, 2002

(65) Prior Publication Data
US 2003/0138961 A1 Jul. 24, 2003

(30) Foreign Application Priority Data
Mar. 2, 2001 (IT) .................................. TO2001A0189

(51) Int. Cl.[7] ............................................. G01N 33/72
(52) U.S. Cl. ................. 436/66; 436/147; 436/148; 436/164; 436/165; 422/82.05; 422/82.09; 422/82.12; 422/82.13; 356/39; 356/40
(58) Field of Search .......................... 436/63, 66, 147, 436/148, 164, 165; 422/82.05, 82.09, 82.12, 82.13; 356/39, 40; 600/320, 328; 435/287.1

(56) References Cited

U.S. PATENT DOCUMENTS

| | | | | |
|---|---|---|---|---|
| 5,601,080 A | * | 2/1997 | Oppenheimer | 600/322 |
| 5,939,640 A | * | 8/1999 | Hauser | 73/727 |
| 6,041,246 A | * | 3/2000 | Krivitski et al. | 600/322 |
| 6,246,894 B1 | * | 6/2001 | Steuer et al. | 600/322 |
| 6,510,330 B1 | * | 1/2003 | Enejder | 600/322 |
| 6,611,320 B1 | * | 8/2003 | Lindberg et al. | 356/40 |

FOREIGN PATENT DOCUMENTS

| | | |
|---|---|---|
| EP | 0 575 712 A2 | 12/1993 |
| IT | 1 240 489 | 12/1993 |
| WO | WO 01/17420 A1 | 3/2001 |
| WO | 01/45770 | * 6/2001 |
| WO | 02/098492 | * 12/2002 |

* cited by examiner

*Primary Examiner*—Maureen M. Wallenhorst
(74) *Attorney, Agent, or Firm*—Finnegan, Henderson, Farabow, Garrett & Dunner, L.L.P.

(57) ABSTRACT

A method for measuring the hemoglobin concentration in the blood in a circuit of a dialysis machine includes directing electromagnetic waves against one section of the circuit, measuring values of the electromagnetic waves transmitted through the section, and determining values of absorption of electromagnetic waves by the blood along the section from the measured values of transmitted electromagnetic waves. The values of absorption are correlated with the values of the hemoglobin concentration. The method also includes measuring the values of at least one physical quantity of the blood, wherein the at least one physical quantity is selected from blood pressure and blood temperature, and calculating the values of hemoglobin concentration as a function of the values of absorption and the at least one physical quantity.

28 Claims, 4 Drawing Sheets

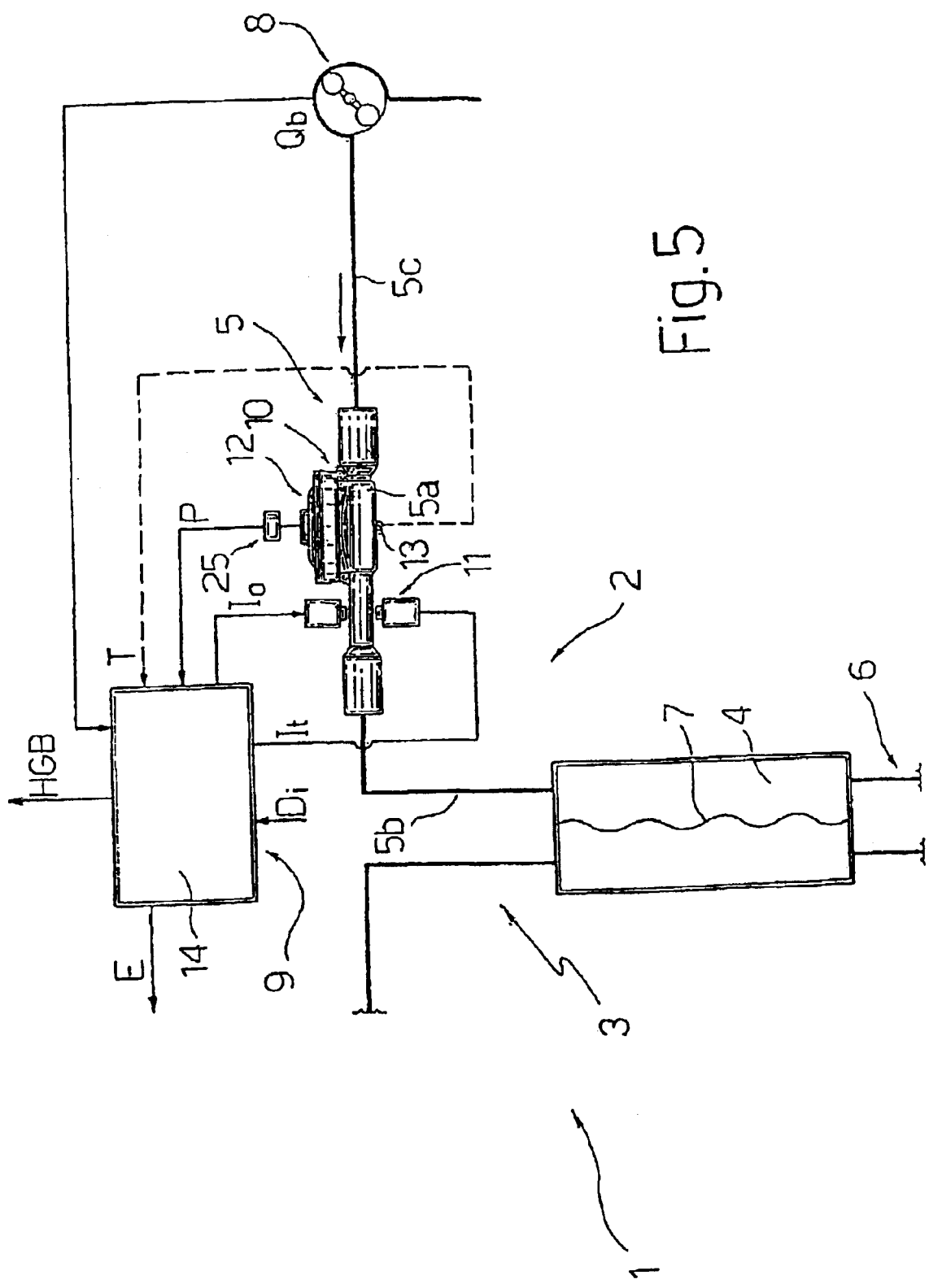

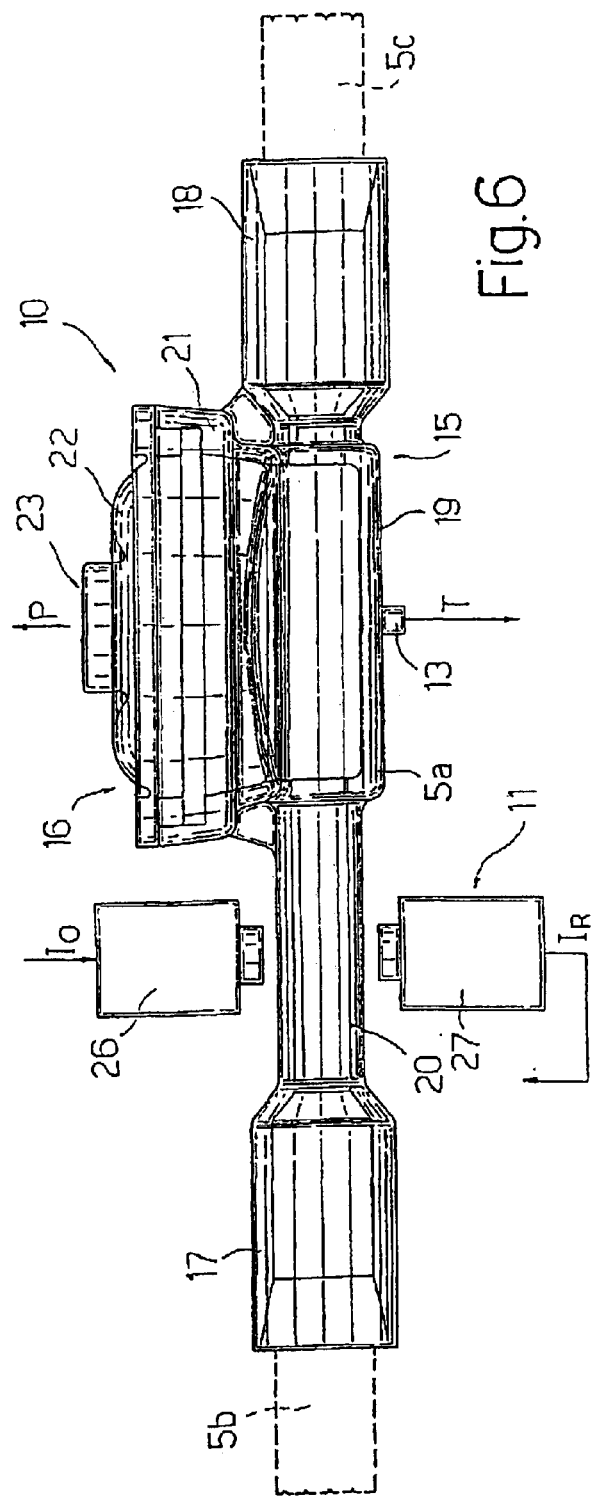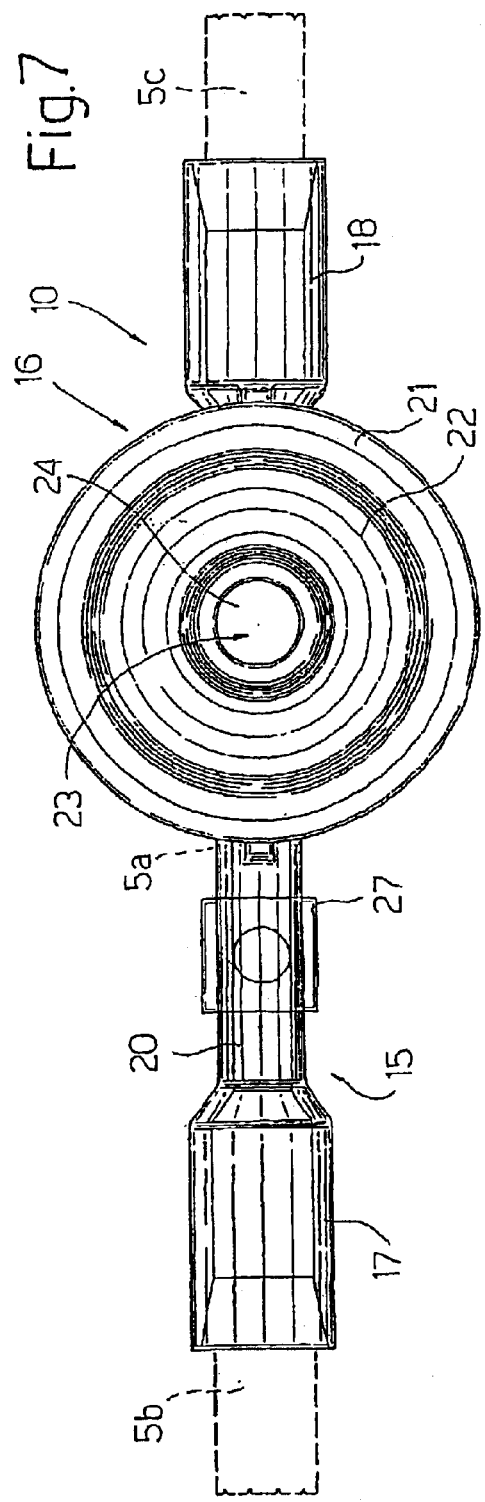

METHOD FOR MEASURING HEMOGLOBIN CONCENTRATION (HGB) IN THE BLOOD IN A CIRCUIT OF A DIALYSIS MACHINE, MEASURING DEVICE AND CIRCUIT FOR THE APPLICATION OF THE METHOD

BACKGROUND OF THE INVENTION

The present invention relates to a method for measuring hemoglobin concentration in the blood in a circuit of a dialysis machine.

Generally, a dialysis machine of the known type comprises a first circuit for blood circulation, connected, when in use, to the circulatory system of a patient, a second circuit for the circulation of dialysate, and a filter, through which the first circuit passes the blood and the second circuit passes the dialysate. The filter comprises a semi-permeable membrane which, when in use, separates the dialysate from the blood, and permits an exchange of ions between the dialysate and the blood and the transfer of some of the blood plasma through the membrane. The first circuit comprises an arterial branch located up-line from the filter and a venous branch located down-line from the filter, while the machine comprises a peristaltic pump located in the arterial branch to convey the blood extracted from the patient to the filter. The first and second circuits are made from transparent flexible material, such as PVC, to ensure the asepsis of the circuit. The flexibility of the circuits facilitates their packaging and enables the flow to be blocked by a simple constriction of a section of the circuit, while the transparency makes it possible to visually inspect the liquids being conveyed in the circuit during use There is a known way of determining the concentration of hemoglobin in the red corpuscles during the dialysis treatment, by means of highly accurate measurements of an intrusive kind, which require the laboratory examination of blood samples. Other dialysis machines enable non-intrusive measurements of the hemoglobin concentration to be made within the machine. The non-intrusive measurements made within the machine are markedly less accurate than laboratory measurements, but have the advantage of being provided in real time in such a way that the operating parameters of the dialysis machine can be corrected instantaneously.

The patent IT 1,240,489 discloses a method of measuring the hemoglobin concentration within the machine and in a non-intrusive way, by measuring the absorption of electromagnetic waves of the blood flowing in the arterial branch of the first circuit.

Hemoglobin is a protein contained in the red corpuscles, and its concentration modifies the pigmentation of the red corpuscles; the concentration of hemoglobin in the blood therefore depends on the quantity of red corpuscles contained in the blood and on the quantity of hemoglobin contained in the red corpuscles. To measure the absorption of electromagnetic waves by the blood, an emitter is used to emit a beam of electromagnetic waves having an emission intensity correlated with an emission signal, the beam of electromagnetic waves is made to strike a section of the circuit, and a beam of electromagnetic waves is detected by means of a receiver which emits a signal correlated with the reception intensity. The difference between the emitted intensity and the received intensity corresponds to the absorption, which is correlated with the hemoglobin concentration by a specific function.

Although the described method has been shown to provide an accurate measurement, laboratory tests conducted by the applicant have demonstrated that, in some cases of operation of the dialysis machine, the measurement made according to the method described above supplies values of hemoglobin concentration which deviate from the concentration values measured in the laboratory for the same type of blood.

The object of the present invention is to provide a method for measuring the hemoglobin concentration in the blood in a circuit of a dialysis machine in a non-intrusive way, and with a level of accuracy which is as close as possible to the level of accuracy of laboratory measurement.

SUMMARY OF A FEW ASPECTS OF THE INVENTION

According to the present invention, a method is provided for measuring the hemoglobin concentration in the blood in a circuit of a dialysis machine, the method comprising the measurement of the absorption of electromagnetic waves by the blood along one section of the said circuit, the values of the said absorption being correlated with the values of the said hemoglobin concentration; the method being characterized in that the values of at least one physical quantity of the blood, from the group comprising blood pressure, blood temperature and the rate of flow of blood along the said section, are measured, and the values of hemoglobin concentration in the blood are calculated as a function of the values of absorption and of the said physical quantity.

The present invention also relates to a circuit for the application of the aforesaid method.

According to the present invention, a blood circulation circuit for a dialysis machine is provided for the application of the method according to at least one of claims 1 to 12, characterized in that it comprises a connection forming the said section of the circuit, the said connection comprising a tube for subjecting the blood to the measurement of the absorption of electromagnetic waves and a chamber for subjecting the blood to the measurement of pressure.

The present invention relates to a device for measuring a characteristic of the blood in a circuit of a dialysis machine.

According to the present invention, a device is provided for measuring the hemoglobin concentration in a circuit of a dialysis machine comprising a connection forming a section of the said circuit, the said connection comprising a tube along which a measurement is made by means of beams of electromagnetic waves to determine the absorption of the blood, the hemoglobin concentration being correlated with the said absorption, the device being characterized in that it comprises at least one further sensor for measuring one of two quantities, namely the blood pressure and the blood temperature; the hemoglobin concentration being a function of the absorption and of the said quantity.

BRIEF DESCRIPTION OF THE DRAWINGS

The present invention will now be described with reference to the attached drawings, which show, without restrictive intent, an example of embodiment in which

FIG. 5 is a schematic view of a dialysis machine for implementing the method according to the present invention;

FIG. 6 is a side elevation of an element of the device for implementing the present invention;

FIG. 7 is a plan view of the element of FIG. 6;

DETAILED DESCRIPTION OF INVENTION EMBODIMENTS

Figure 2:
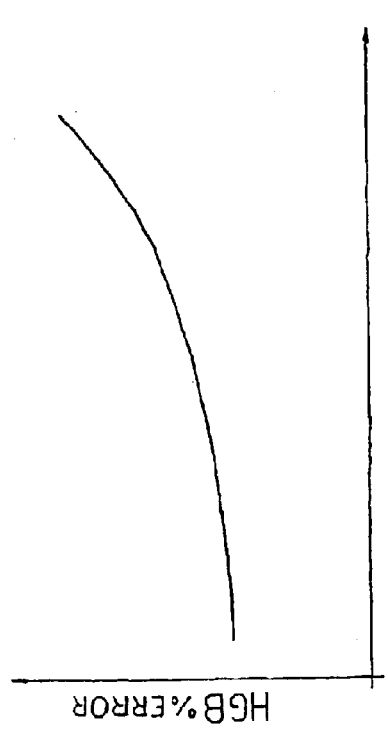
FIG. 2 is an experimental graph showing the error of measurement of the hemoglobin concentration as a function of the blood temperature.

With reference to FIG. 5, the number 1 indicates the whole of a dialysis machine for carrying out dialysis treatments on patients suffering from kidney failure. The machine 1 comprises a blood circuit 2, a dialysate circuit 3, and a filter 4. In use, the circuit 2 is connected to the circulatory system of a patient and supplies the blood taken from the patient to the filter 4 along an arterial branch 5 and returns the blood to the patient along a venous branch 6. The filter 4 comprises a semi-permeable membrane 7, which separates the blood from the dialysate and permits an exchange of ions between the blood and the dialysate and the extraction of some of the blood plasma from the blood circuit 2. The machine 1 comprises a peristaltic pump 8, which is located on the arterial branch 5 and, in use, extracts the blood from the patient and conveys the blood to the filter 4, and a measuring device 9 for measuring hemoglobin concentration (HGB) in the blood along the arterial branch 5 in a non-intrusive way.

Figure 1:
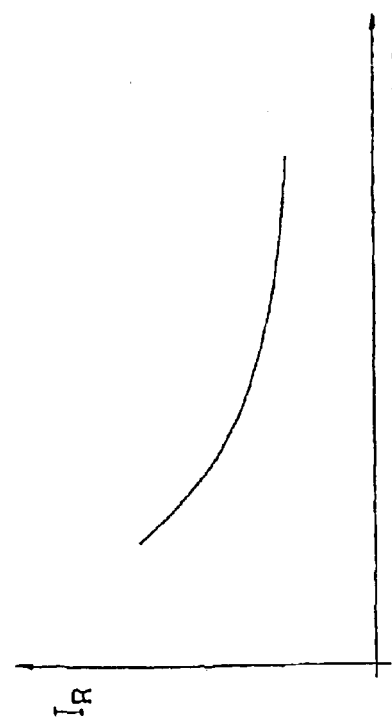
FIG. 1 is an experimental graph showing the hemoglobin concentration as a function of the received intensity.

The measuring device 9 comprises a connection 10 located between the peristaltic pump 8 and the filter 4, a sensor 11 of the optical type, a pressure sensor 12, a temperature sensor 13 and a calculation unit 14 connected to the sensors 11, 12 and 13. With reference to FIG. 1, the connection 10 forms a section 5a of the arterial branch 5 and is interposed between two flexible sections 5b and 5c of the arterial branch 5.

With reference to FIGS. 6 and 7, the connection 10 comprises a tube 15 and a chamber 16 rigidly connected to the tube 15; the tube 15 is integral with the chamber 16 and both are made from transparent rigid plastic. The chamber and/or the tube may integrally carry a radial element protruding from the surface of connection 10 in the form of a little fin (not shown) that may serve to easily handle the connector and as positioning device to easily mount and fix the connector onto a machine. The tube 15 comprises an opening 17 for connection to the section 5b, an opening 18 for connection to the section 5c, a portion 19 adjacent to the chamber 16 and a portion 20, which has an internal diameter Di and is located between the opening 17 and the portion 19. The chamber 16 comprises a container 21, a cover 22 provided with a central hole 23 and an elastic membrane 24, which is gripped between the container 19 and the cover 22 and is deformed as a function of the blood pressure. In other words, the pressure sensor 12 comprises the chamber 16 and an electric device 25 for measuring the extent of deformation of the membrane 24 in the form of an electrical signal acquired by the control unit 14.

The sensor 11 comprises an emitter 26 for emitting a beam of electromagnetic waves in the visible, or "NIR", spectrum, and for guiding the beam of electromagnetic waves along the portion 18 of the tube 14 and a detector 27 for receiving a beam of electromagnetic waves on the opposite side of the tube 14. The sensor 11 is described in detail in the patent IT 1,240,489, whose content is included by reference in the present description.

The temperature (T) sensor 13 is a sensor of electromagnetic waves which are outside the visible or NIR spectrum.

In use, the peristaltic pump 8 provides a flow of blood $Q_b$ along the circuit 2 as indicated by the arrow in FIG. 1 and through the connection 10. The peristaltic pump 8 supplies the values of the flow $Q_b$ to the controller 13 at successive instants.

The sensor 12 transmits electrical signals correlated to the pressure values P at successive instants to the calculation unit 14, while the sensor 13 supplies electrical signals correlated with the values of temperature T to the calculation unit 14. The blood flowing along the portion 20 of the tube 15 forms an optical path which is correlated with the internal diameter Di of the portion 20, while the detector 27 receives a beam of electromagnetic waves on the opposite side of the portion 20. The emitted beam is correlated with a signal of emitted intensity $I_0$ and the received beam generates a signal of received intensity $I_R$ The calculation unit 14 receives, in a time sequence with constant intervals, the values of the received intensity $I_R$ for a constant emitted intensity $I_0$. In practice, the absorption A is equal to the emitted intensity $I_0$ minus the received intensity $I_R$.

The measurement of the hemoglobin concentration HGB is based on studies carried out by the applicant, who, by means of experimental tests, has correlated the hemoglobin concentration HGB with the absorption A, in other words with the received intensity signal $I_R$ for a constant emitted intensity signal $I_0$, as shown in the graph of FIG. 1.

Figure 4:
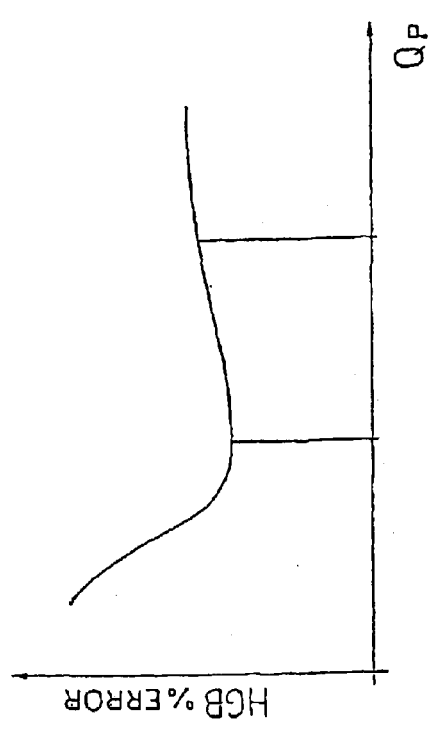
FIG. 4 is an experimental graph showing the error of measurement of the hemoglobin concentration as a function of the blood flow.
Figure 3:
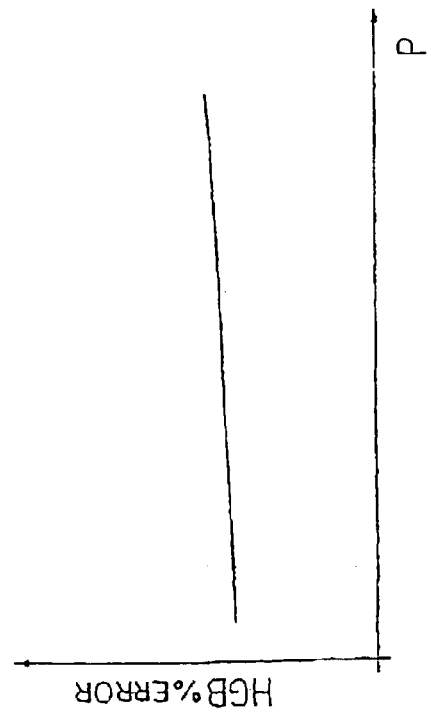
FIG. 3 is an experimental graph showing the error of measurement of the hemoglobin concentration as a function of the blood pressure.

The applicant has determined the error of measurement of the hemoglobin concentration HGB as a function of the blood pressure P as shown in FIG. 3, as a function of the blood flow $Q_b$ as shown in FIG. 4, and as a function of temperature T as shown in FIG. 2.

The applicant's studies have demonstrated that the blood flow $Q_b$, the pressure P, and the temperature T modify the blood's capacity for absorption (A) of electromagnetic radiation, in other words the absorption A, and cause a deviation between the values of hemoglobin concentration HGB found in the machine and those found in laboratory tests. In other words, the physical quantities acting on the blood during the operation of the machine 1 cause structural modifications of the red corpuscles, which, although small, are sufficient to alter the measurement of the hemoglobin concentration HGB. In particular, when the pressure P increases the red corpuscles are flattened, while the flow $Q_b$ causes an orientation of the red corpuscles and the temperature T causes a change in the dimensions of the corpuscles.

Measurements were made on the basis of the studies carried out by the applicant, and by means of the measuring device 9, and their accuracy was found to increase with an increase in the allowance made for the physical quantities which modify the structure of the red corpuscles.

The value of the internal diameter Di is set in the calculation unit 14, which receives the value of the flow $Q_b$ and calculates the hemoglobin concentration HGB as a function of the values of absorption A of electromagnetic waves, of the pressure values P measured by the sensor 12, of the flow $Q_b$ Of the pump 8, and of the values T measured by the sensor 13.

In practice, the following function relating the hemoglobin concentration to the aforesaid quantities was calculated on the basis of the studies which were carried out:

$$HGB = \left(\ln\frac{I_R}{I_0}\right) \cdot f\left(Q_i, P, Di, T\right) = \left[\ln\left(1 - \frac{A}{I_0}\right)\right] \cdot f(Q_B, P, Di, T)$$

This function can also be simplified, since eliminating the dependence on one or two of the measured physical quantities, consisting of the pressure P, the flow $Q_b$ and the temperature T, will provide a measurement of the hemoglobin concentration HGB which is less accurate than the measurement in which the function takes into account all three of the measured physical quantities, but is still more accurate than a measurement based solely on the absorption A, and is closer to the laboratory measurements.

The structure and functional working of the connection 10 is important in order to properly compensate the measurement of HGB as a function of the pressure. Indeed the amplitude, period and variable components of pressure in the tube 15 (the pressure is constantly modulated by the blood pump 8) influence the HGB measurement. Since the tube 15 and the chamber 16 are directly engaged one another and both made of rigid material the pressure detection in the chamber 16 is very precise and strictly related to the pressure and to the pressure variations in tube 15. Moreover, given the close proximity between tube 15 and chamber 16 and the rigidity of connection 10, it is practically impossible to deform the blood conduit between the section where the optical detection is carried out and the section where the pressure detection is obtained. The axial distance between the cross section of the portion 20 of tube 15 where the optical detection is carried out and the cross section of chamber 16 where the pressure detection is obtained shall be less than 50 mm; in the embodiment shown in the FIGS. 6 and 7 such a distance is equal to 25 mm. The portion 20 of tube 15 shall present an internal diameter Di less than 10 mm.

Figure 8:
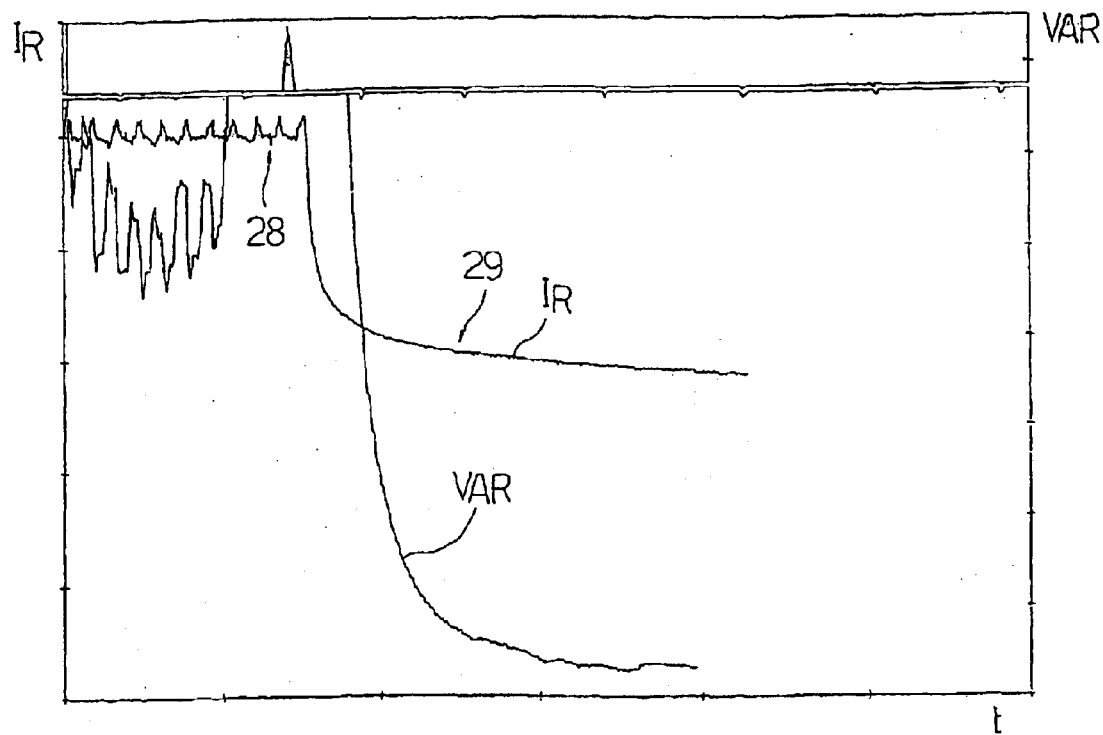
FIG. 8 is a graph of received intensity as a function of time in a first operating condition of the machine of FIG. 5.
Figure 9:
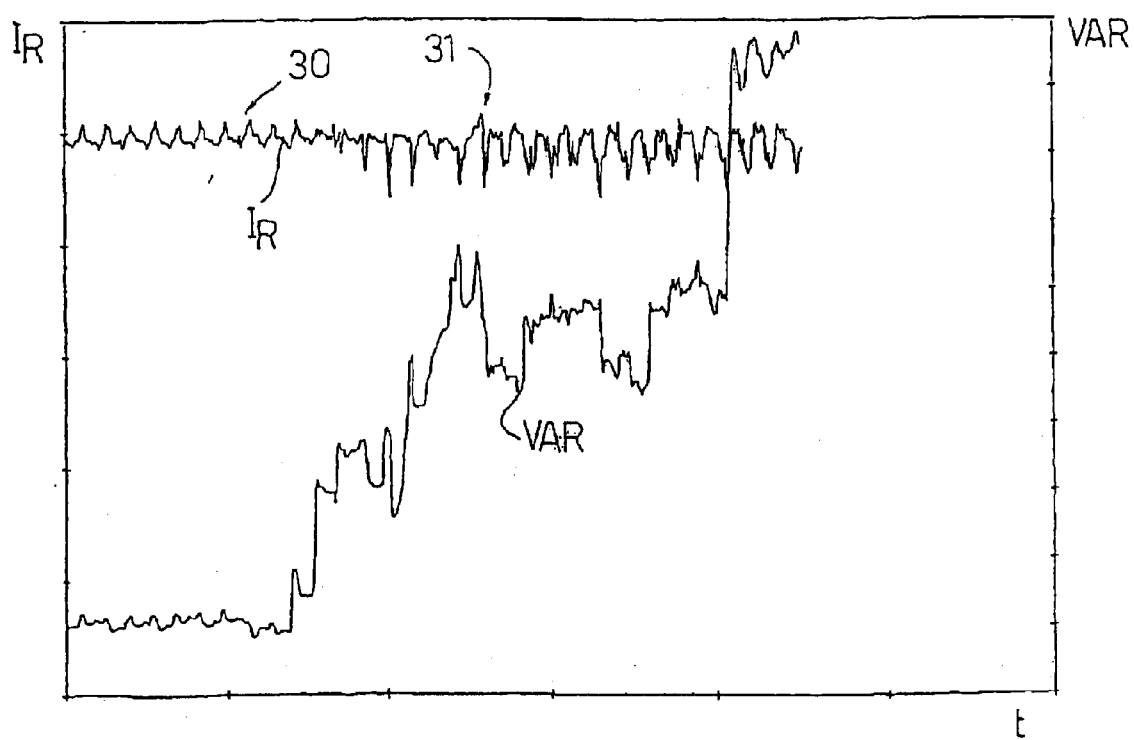
FIG. 9 is a graph of received intensity as a function of time in a second operating condition of the machine of FIG. 5.

With reference to FIGS. 8 and 9, the graphs show a curve of the intensity $I_R$ received by the detector 27 as a function of time t and a curve of the values of the variance VAR of the curve of received intensity $I_R$ as a function of time t.

With reference to FIG. 8, the curve of the values of $I_R$ comprises a first section 28, which is characterized by a cyclical variation of the values of $I_R$ caused by the flow $Q_b$ provided by the peristaltic pump 8 and corresponds to a normal stage of operation of the dialysis machine 1, and a section 29 which corresponds to a stage in which a blockage of the circuit has occurred up-line from the sensor 11. Although the divergence between the values of $I_R$ of the section 28 and those of the section 29 is significant in graphic terms, it is difficult, in terms of the signal, to establish a threshold which clearly distinguishes the section 28 from the section 29. Conversely, the variance VAR shows a peak tending towards infinity at the point of the change from the section 28 to the section 29, in other words at the instant when the blockage of the circuit 2 occurs.

With reference to FIG. 9, the curve of the received intensity $I_R$ comprises a first section 30 which corresponds to a stage of normal operation of the machine 1, and a section 31 which corresponds to a stage in which a blockage of the circuit has occurred down-line from the sensor 11, which does not cause a significant variation of the received intensity $I_R$. Conversely, the down-line blockage causes a significant variation of the variance VAR as a function of time t.

The calculation unit 14 constantly compares each value of the variance VAR with a range of acceptability in the region of a mean value of the values of variance VAR corresponding to the normal operation of the machine 1, in other words without blockages of the circuit 2. If the value of the variance VAR diverges significantly from the range of acceptability, the calculation unit 14 emits an error signal E.

Consequently, the measurement of the absorption A is used not only to measure the hemoglobin concentration HGB, but also to discover whether a blockage has occurred up-line or down-line from the sensor 11 in the arterial branch 5.

What is claimed is:

1. Method of measuring the hemoglobin concentration in blood in a circuit of a dialysis machine, the method comprising the steps of:
    directing electromagnetic waves against one section of said circuit;
    measuring values of the electromagnetic waves transmitted through said section;
    determining values of absorption of electromagnetic waves by the blood along said section from said measured values of transmitted electromagnetic waves, the values of said absorption being correlated with values of said hemoglobin concentration;
    measuring values of at least one physical quantity of the blood, said at least one physical quantity being selected from blood pressure and blood temperature; and
    calculating the values of hemoglobin concentration as a function of the values of absorption and of said at least one physical quantity.

2. Method according to claim 1, wherein the values of hemoglobin concentration are calculated as a function of the values of absorption and the values of blood pressure measured along said section.

3. Method according to claim 1, wherein the values of hemoglobin concentration are calculated as a function of the values of absorption and the values of blood temperature measured along said section.

4. Method according to claim 1, wherein said section is located downstream from a peristaltic pump providing a specified blood flow rate.

5. Method according to claim 1, wherein the values of hemoglobin concentration are calculated as a function of the values of absorption, the values of blood pressure and values of blood flow rate along said section.

6. Method according to claim 1, wherein the values of hemoglobin concentration being calculated as a function of the values of absorption, values of blood pressure, values of blood flow rate, and values of blood temperature.

7. Method according to claim 1, wherein said section comprises a portion of a tube, said electromagnetic waves passing through said portion along a specified path.

8. Method according to claim 7, wherein said path is correlated with an internal diameter of said portion.

9. Method according to claim 8, wherein the hemoglobin concentration in the blood is calculated as a function of said internal diameter of said portion.

10. Method according to claim 1, wherein absorption is measured by means of a sensor located in said section, comprising an emitter for emitting a beam of electromagnetic waves with a specified emission intensity and a detector which can detect a received intensity.

11. Method according to claim 10, wherein said absorption is equal to a difference between the emission intensity and the received intensity.

12. Method according to claim 10, wherein said detector is arranged on an opposite side of said section with respect to said emitter.

13. Method according to claim 10, wherein a variance of said received intensity is calculated, and said variance is compared with a range of acceptability to detect an interruption at least one of upstream and downstream from said section.

14. Method according to claim 13, wherein an error signal is emitted if the value of said variance is outside said range of acceptability.

15. Blood circulation circuit for a dialysis machine, comprising a connection including a tube for subjecting blood to a measurement of absorption of electromagnetic waves and a chamber for subjecting the blood to a measurement of pressure, said chamber being at least one of rigidly connected to, directly engaged with, and integral with said tube.

16. Blood circuit according to claim 15, wherein said tube and said chamber are both made of rigid material.

17. Blood circuit according to claim 15, wherein said chamber is covered by a deformable membrane.

18. Blood circuit according to claim 15, comprising an arterial branch and a venous branch, said connection being located along said arterial branch.

19. Blood circuit according to claim 15, wherein said tube includes a portion defining a first measurement cross section where the absorption measurement is carried out, and said chamber includes a second measurement cross section where pressure detection is obtained, a distance between said measurement cross sections being less than 50 mm.

20. Blood circuit according to claim 19, wherein said tube portion has an internal diameter less than 10 mm.

21. Device for measuring hemoglobin concentration of blood in a circuit of a dialysis machine, comprising:
  a connection forming a section of said circuit, said connection comprising a tube along which a measurement is made by means of beams of electromagnetic waves to determine absorption of the blood, the hemoglobin concentration being correlated with said absorption;
  at least one temperature sensor located in said connection for measuring blood temperature, the hemoglobin concentration being a function of absorption and of blood temperature.

22. Device according to claim 21, comprising a calculation unit connected to said temperature sensor, to an absorption sensor located on said tube, and to a peristaltic pump providing a blood flow rate along said tube, the hemoglobin concentration further being a function of blood flow rate.

23. Device for measuring hemoglobin concentration of blood in a circuit of a dialysis machine, comprising:
  a connection forming a section of said circuit, said connection comprising a tube along which a measurement is made by means of beams of electromagnetic waves to determine absorption of the blood, the hemoglobin concentration being correlated with said absorption;
  at least one pressure sensor for measuring blood pressure, said pressure sensor being at least one of rigidly connected to, directly engaged with, and integral with said tube, the hemoglobin concentration being a function of absorption and of blood pressure.

24. Device according to either claim 21 or 23, wherein said connection is located downstream from a peristaltic pump providing a specified rate of flow of blood.

25. Device according to claim 23, wherein said pressure sensor comprises a chamber fitted with a deformable membrane to measure the variations of pressure of the blood by means of an electrical device in said section.

26. Device according to claim 25, wherein said tube and said chamber are made from rigid material.

27. Device according to either claim 21 or 23, comprising an absorption sensor located on said tube, said absorption sensor comprising an emitter for emitting a beam of electromagnetic waves with a specified emission intensity against said tube and a detector which can detect a received intensity, said absorption being equal to a difference between said emission intensity and said received intensity.

28. Device according to claim 23, comprising a calculation unit connected to said pressure sensor, to an absorption sensor located on said tube, and to a peristaltic pump providing a blood flow rate along said tube, the hemoglobin concentration further being a function of blood flow rate.

* * * * *